(12) United States Patent
Fuchigami et al.

(10) Patent No.: US 6,476,267 B1
(45) Date of Patent: Nov. 5, 2002

(54) PROCESS FOR PRODUCING AROMATIC PRIMARY AMINE BY LOW-PRESSURE

(75) Inventors: Takamasa Fuchigami, Kanagawa (JP); Satoshi Takamizawa, Kanagawa (JP); Noriko Wakasa, Kanagawa (JP)

(73) Assignee: Sagami Chemical Research Center, Kanagawa (JP)

( * ) Notice: Subject to any disclaimer, the term of this patent is extended or adjusted under 35 U.S.C. 154(b) by 0 days.

(21) Appl. No.: 09/890,935

(22) PCT Filed: Feb. 3, 2000

(86) PCT No.: PCT/JP00/00586

§ 371 (c)(1),
(2), (4) Date: Nov. 19, 2001

(87) PCT Pub. No.: WO00/46179

PCT Pub. Date: Aug. 10, 2000

(30) Foreign Application Priority Data

Feb. 4, 1999 (JP) .............................................. 11-026887
Jun. 3, 1999 (JP) .............................................. 11-156052

(51) Int. Cl.$^7$ .............................................. C07C 253/30
(52) U.S. Cl. ........................ 564/385; 564/415; 546/329; 546/334
(58) Field of Search ................................ 564/385, 415; 546/329, 334

(56) References Cited

FOREIGN PATENT DOCUMENTS

| JP | 5-97776 A | 4/1993 |
|---|---|---|
| JP | 8-53417 A | 2/1996 |
| WO | WO 98/33765 A1 | 8/1998 |

*Primary Examiner*—Samuel Barts
(74) *Attorney, Agent, or Firm*—Browdy and Neimark

(57) ABSTRACT

A method for producing an aromatic primary amine, characterized by hydrogenating an aromatic nitrile at a low partial pressure of hydrogen in a heterogeneous system comprising a non-reductive polar solvent and a nickel-immobilized catalyst suspended therein was proposed. By such method, an aromatic primary amine which is industrially useful as a medicine, agricultural chemical, dye surfactant, chemical agent, etc. can be produced in a high yield.

16 Claims, No Drawings

PROCESS FOR PRODUCING AROMATIC PRIMARY AMINE BY LOW-PRESSURE

REFERENCE TO RELATED APPLICATIONS

The present application is the national stage under 35 U.S.C. 371 of international application PCT/JP00/00586, filed Feb. 3, 2000 which designated the United States, and which international application was not published under PCT Article 21(2) in the English language.

FIELD OF THE INVENTION

The present invention relates to a method for producing an aromatic primary amine in a high yield in which an aromatic nitrile is hydrogenated under a low pressure condition.

BACKGROUND ART

Aromatic amine is a useful compound as an industrial raw material, and is utilized in a variety of field such as those of medicine, agricultural chemical, dye, surfactant and chemical agent. Many proposals have been made as for methods for producing primary amine by hydrogenation of aliphatic nitrile. On the contrary, it is well known in the art that production of primary amine through hydrogenating aromatic nitrile is much more difficult than starting from aliphatic nitrile, since hydrogenation of the aromatic ring may proceed, or a large amount of secondary amine may be by-produced. In fact, only four methods described below have ever been proposed, in which aromatic nitrites employed are limited to those having no substituent on the aromatic ring, such as benzonitrile, 3-cyanopyridine and isophthalonitrile.

(1) Japanese Kokai Tokkyo Koho 62-129257 discloses a method in which benzonitrile is reduced using Raney nickel or Raney cobalt in the presence of ammonia. It is, however, difficult to practice such method on the industrial basis since it requires a hydrogen pressure extremely as high as 100 kg/cm$^2$G.

(2) U.S. Pat. No. 4,254,059 discloses a method in which benzonitrile is hydrogenated using a ruthenium-phosphine complex catalyst. Such method is again not applicable on the economical and industrial basis, since ruthenium is a kind of noble metals, phosphine as a ligand is also expensive, and 18-crown-6 used as an additive is still also expensive.

(3) Japanese Kokai Tokkyo Koho 05-097776 discloses a method in which benzonitrile and 3-cyanopyridine are hydrogenated using a cobalt-immobilized alumina catalyst and a rhodium-immobilized silica catalyst. Both of rhodium and cobalt are, however, kinds of noble metals and are less acceptable on the economical basis. Another problem resides in that the method uses a large amount of ammonia as a solvent, which inevitably promotes elution of the catalytic metals to thereby shorten the lifetime of such catalysts, and is again less acceptable on the industrial basis. While the specification exemplifies a case in which succinonitrile, one of aliphatic nitrites, is hydrogenated using a nickel-silica catalyst, the use of nickel amounts as much as 54.4 mol % of the substrate, which indicates an extremely low catalytic efficiency.

(4) U.S. Pat. No. 3,069,469 proposes a method in which isophthalonitrile is hydrogenated using a cobalt-nickel catalyst. The method, however, requires for the reaction a hydrogen pressure extremely as high as 175 to 245 kg/cm$^2$G, which is not practical on the industrial basis.

DISCLOSURE OF THE INVENTION

An object of the present invention resides in that overcoming a number of the foregoing problems inherent to the prior art, and that providing a method for producing an aromatic primary amines in a high yield by hydrogenating an aromatic nitrile at a low pressure. The present inventors found after extensive studies that hydrogenation under a specific condition using a nickel-immobilized catalyst can successfully produce an aromatic primary amine at a low temperature, which led us to propose the present invention.

That is, the present invention relates to a method for producing an aromatic primary amine, characterized by hydrogenating an aromatic nitrile at a low partial pressure of hydrogen in a heterogeneous system comprising a non-reductive polar solvent and a nickel-immobilized catalyst suspended therein.

The present invention will be detailed hereinafter.

BEST MODES FOR CARRYING OUT THE INVENTION

The aromatic nitrile in the context of the present invention include aromatic polynitriles having on a single aromatic ring a plurality of cyano groups, such as phthalonitrile, isophthalonitrile and terephthalonitrile. The term "aromatic" in the present invention is used for expressing compounds having hydrocarbon-base aromatic group and heterocyclic aromatic ring, which are exemplified by those having phenyl group, naphthyl group, anthryl group, pyridyl group, furyl group or thienyl group, where all of such groups may be substituted by one or more substituents not responsible for the reaction. Examples of such substituent not responsible for the reaction include alkyl group, aromatic group, alkoxy group, phenoxy group, alkylthio group, phenylthio group, silyl group, silyloxy group, halogen atom, nitro group, amino group, amide group, hydroxyl group and composite group based on the combination of two or more thereof. For the case having two or more substituents, such substituents may differ with each other. The composite group based on the combination of two or more thereof include alkoxyalkyl group, halogenated alkyl group, silylated aromatic group, nitrophenoxy group, and N,N-dialkylamino group. While it is generally known that reactivity in the hydrogenation of aromatic nitrile largely depends on the substituents on the aromatic ring, the reaction in the present invention can proceed with a high efficiency even in the presence of such substituents.

The nickel-immobilized catalyst in the present invention refers to a catalyst which comprises a carrier and nickel immobilized thereon. The available carrier can be such that comprising a porous material, which is typified by metal oxide, composite oxide, layered clay compound and activated carbon. From the viewpoints of catalytic activity and reaction efficiency, particularly preferable examples thereof include silica, alumina, activated carbon, and arbitral combinations thereof. There is no limitation on processes for producing such immobilized catalysts, and any of those produced by known processes are available. That is, the catalyst may be produced by immersion process, ion exchange process and physical mixing process. While the amount of immobilization of catalytic metal is not specifically limited, it can generally be selected within a range from 1 to 80 wt % of the total amount of the catalyst. The amount of use of the catalyst depends on the amount of immobilization of catalytic metal and is not specifically limited, where the amount of nickel can generally be selected within a range from 0.01 to 40 mol % of aromatic nitrile as the substrate, and more preferably from 0.1 to 20 mol % from the viewpoints of reaction efficiency and economy.

The non-reductive polar solvent in the present invention refers to polar solvents not reducible by hydrogen during the reaction, and examples of which include alcoholic solvents such as methanol, ethanol, propanol, isopropyl alcohol, t-butyl alcohol, ethylene glycol, Methyl Cellosolve and phenol; ether solvents such as diethyl ether, tetrahydrofuran, dioxiane and dimethoxyethane; and water. Among which, the alcoholic solvents are preferable in terms of reaction efficiency, yield, selectivity and convenience for recovery and isolation of the product.

In the present invention, the reaction is proceeded under heated and pressurized conditions. There is no special limitation on the reaction method, and the reaction may be proceeded in a batch manner or semi-batch manner. The partial pressure of hydrogen is generally selected within a range from 0.1 to 50 kg/cm$^2$G, where a preferable range considering safety and economy is 19 kg/cm$^2$G or below, and more preferably 10 kg/cm$^2$G or below. The reaction temperature can generally be selected within a range from room temperature to 200° C., where a preferable range considering reaction efficiency, safety and economy is 80 to 150° C.

The reaction in the present invention may be proceeded in the presence of ammonia. The presence of ammonia tends to raise the selectivity and yield. There is no special limitation on the amount of use of ammonia, it is preferably selected in general within a range from 1 to 20 mol equivalence of aromatic nitrile as the substrate, and more preferably within a range from 1 to 4 mol equivalence in terms of the reaction efficiency, yield and selectivity.

The method of the present invention will further be detailed hereinafter based on preferred Examples. It should now be noted that the present invention is by no means limited to such Examples.

EXAMPLES

Example 1

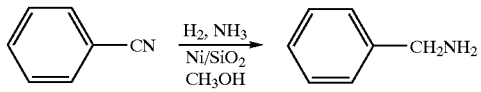

In a 50-ml autoclave with an electromagnetic stirring mechanism, 1.03 g (10 mmol) of benzonitrile, 10 ml of a 2M ammoniacal methanol solution (ammonia 20 mmol) and 50 mg (0.5 mmol) of a 60 wt % nickel-silica were weighed, and hydrogen gas was introduced at 5 kg/cm$^2$G. The mixture was quickly heated to 120° C., and stirred while gradually supplying hydrogen so as to keep the total pressure at 10 kg/cm$^2$G. Six hours after, the reaction was terminated, the catalyst was removed by filtration, and the collected reaction solution was analyzed by gas chromatography, which revealed the production of benzylamine in a 99.2% yield.

Example 2

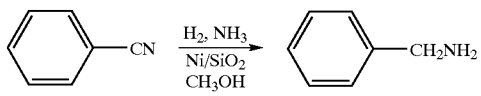

In a 50-ml autoclave with an electromagnetic stirring mechanism, 1.03 g (10 mmol) of benzonitrile, 10 ml of a 2M ammoniacal methanol solution (ammonia 20 mmol) and 10 mg (0.1 mmol) of a 60 wt % nickel-silica were weighed, and hydrogen gas was introduced at 5 kg/cm$^2$G. The mixture was quickly heated to 120° C., and stirred while gradually supplying hydrogen so as to keep the total pressure at 10 kg/cm$^2$G. Six hours after, the reaction was terminated, the catalyst was removed by filtration, and the collected reaction solution was analyzed by gas chromatography, which revealed the production of benzylamine in a 95.7% yield.

Example 3

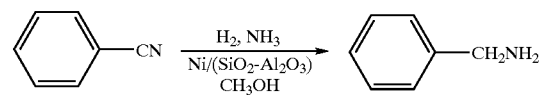

In a 50-ml autoclave with an electromagnetic stirring mechanism, 1.03 g (10 mmol) of benzonitrile, 10 ml of a 2M ammoniacal methanol solution (ammonia 20 mmol) and 50 mg (0.5 mmol) of a 65 wt % nickel-silica alumina were weighed, and hydrogen gas was introduced at 5 kg/cm$^2$G. The mixture was quickly heated to 120° C., and stirred while gradually supplying hydrogen so as to keep the total pressure at 10 kg/cm$^2$G. Six hours after, the reaction was terminated, the catalyst was removed by filtration, and the collected reaction solution was analyzed by gas chromatography, which revealed the production of benzylamine in a 96.1% yield.

Example 4

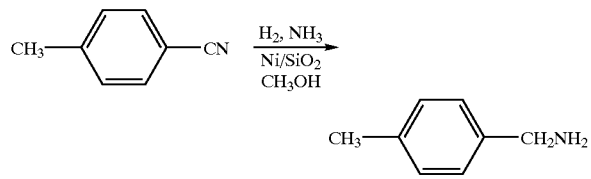

In a 50-ml autoclave with an electromagnetic stirring mechanism, 1.17 g (10 mmol) of 4-tolunitrile, 10 ml of a 2M ammoniacal methanol solution (ammonia 20 mmol) and 50 mg (0.5 mmol) of a 60 wt % nickel-silica were weighed, and hydrogen gas was introduced at 5 kg/cm$^2$G. The mixture was quickly heated to 120° C., and stirred while gradually supplying hydrogen so as to keep the total pressure at 10 kg/cm$^2$G. Six hours after, the reaction was terminated, the catalyst was removed by filtration, and the collected reaction solution was analyzed by gas chromatography, which revealed the production of 4-methylbenzylamine in a 99.3% yield.

Example 5

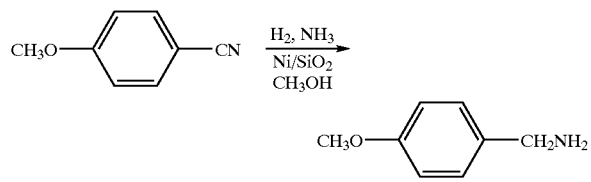

In a 50-ml autoclave with an electromagnetic stirring mechanism, 1.33 g (10 mmol) of 4-methoxybenzonitrile, 10 ml of a 2M ammoniacal methanol solution (ammonia 20 mmol) and 50 mg (0.5 mmol) of a 60 wt % nickel-silica were weighed, and hydrogen gas was introduced at 5 kg/cm²G. The mixture was quickly heated to 120° C., and stirred while gradually supplying hydrogen so as to keep the total pressure at 10 kg/cm²G. Six hours after, the reaction was terminated, the catalyst was removed by filtration, and the collected reaction solution was analyzed by gas chromatography, which revealed the production of 4-methoxybenzylamine in a 96.9% yield.

Example 6

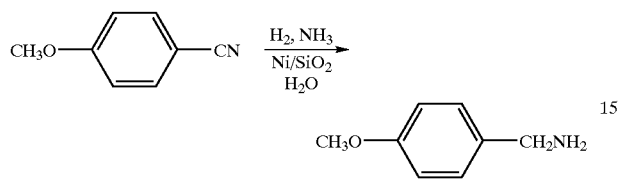

In a 50-ml autoclave with an electromagnetic stirring mechanism, 1.33 g (10 mmol) of 4-methoxybenzonitrile, 10 ml of a 2.5% ammonia solution (ammonia 15 mmol) and 50 mg (0.5 mmol) of a 60 wt % nickel-silica were weighed, and hydrogen gas was introduced at 5 kg/cm²G. The mixture was quickly heated to 120° C., and stirred while gradually supplying hydrogen so as to keep the total pressure at 10 kg/cm²G. Six hours after, the reaction was terminated, the catalyst was removed by filtration, and the collected reaction solution was analyzed by gas chromatography, which revealed the production of 4-methoxybenzylamine in a 92.1% yield.

Example 7

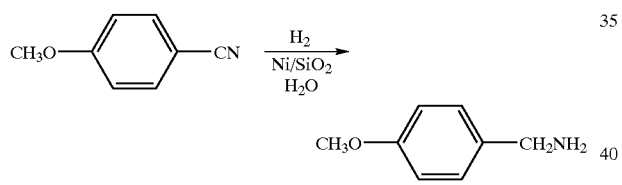

In a 50-ml autoclave with an electromagnetic stirring mechanism, 1.33 g (10 mmol) of 4-methoxybenzonitrile, 10 ml of water and 50 mg (0.5 mmol) of a 60 wt % nickel-silica were weighed, and hydrogen gas was introduced at 5 kg/cm²G. The mixture was quickly heated to 120° C., and stirred while gradually supplying hydrogen so as to keep the total pressure at 10 kg/cm²G. Six hours after, the reaction was terminated, the catalyst was removed by filtration, and the collected reaction solution was analyzed by gas chromatography, which revealed the production of 4-methoxybenzylamine in a 74.9% yield.

Example 8

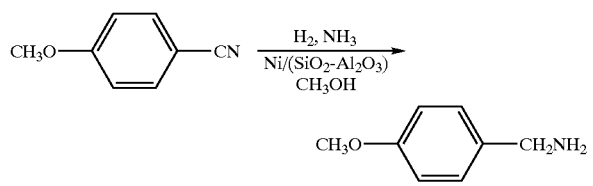

In a 50-ml autoclave with an electromagnetic stirring mechanism, 1.33 g (10 mmol) of 4-methoxybenzonitrile, 10 ml of a 2M ammoniacal methanol solution (ammonia 20 mmol) and 50 mg (0.5 mmol) of a 65 wt % nickel-silica alumina were weighed, and hydrogen gas was introduced at 5 kg/cm²G. The mixture was quickly heated to 120° C., and stirred while gradually supplying hydrogen so as to keep the total pressure at 10 kg/cm²G. Six hours after, the reaction was terminated, the catalyst was removed by filtration, and the collected reaction solution was analyzed by gas chromatography, which revealed a quantitative production of 4-methoxybenzylamine.

Example 9

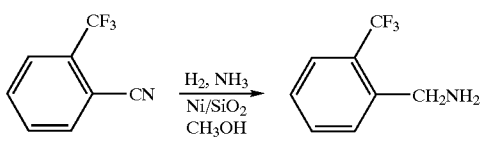

In a 50-ml autoclave with an electromagnetic stirring mechanism, 1.71 g (10 mmol) of 2-trifluoromethylbenzonitrile, 10 ml of a 2M ammoniacal methanol solution (ammonia 20 mmol) and 50 mg (0.5 mmol) of a 60 wt % nickel-silica were weighed, and hydrogen gas was introduced at 5 kg/cm²G. The mixture was quickly heated to 120° C., and stirred while gradually supplying hydrogen, so as to keep the total pressure at 10 kg/cm²G. Six hours after, the reaction was terminated, the catalyst was removed by filtration, and the collected reaction solution was analyzed by gas chromatography, which revealed the production of 2-trifluoromethylbenzylamine in a 96.9% yield.

Example 10

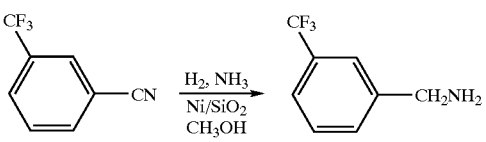

In a 50-ml autoclave with an electromagnetic stirring mechanism, 1.71 g (10 mmol) of 3-trifluoromethylbenzonitrile, 10 ml of a 2M ammoniacal methanol solution (ammonia 20 mmol) and 50 mg (0.5 mmol) of a 60 wt % nickel-silica were weighed, and hydrogen gas was introduced at 5 kg/cm²G. The mixture was quickly heated to 120° C., and stirred while gradually supplying hydrogen so as to keep the total pressure at 10 kg/cm²G. Six hours after, the reaction was terminated, the catalyst was removed by filtration, and the collected reaction solution was analyzed by gas chromatography, which revealed the production of 3-trifluoromethylbenzylamine in a 86.5% yield.

Example 11

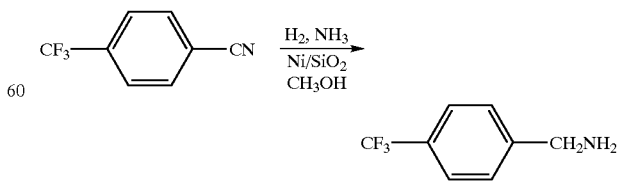

In a 50-ml autoclave with an electromagnetic stirring mechanism, 1.71 g (10 mmol) of 4-trifluoromethylbenzonitrile, 10 ml of a 2M ammoniacal methanol solution (ammonia 20 mmol) and 50 mg (0.5 mmol) of a 60 wt % nickel-silica were weighed, and hydrogen gas was introduced at 5 kg/cm²G. The mixture was quickly heated to 120° C., and stirred while gradually supplying hydrogen so as to keep the total pressure at 10 kg/cm²G. Six hours after, the reaction was terminated, the catalyst was removed by filtration, and the collected reaction solution was analyzed by gas chromatography, which revealed the production of 4-trifluoromethylbenzylamine in a 98.1% yield.

Example 12

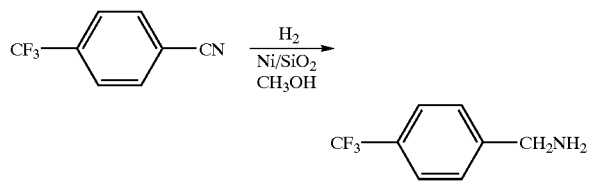

In a 50-ml autoclave with an electromagnetic stirring mechanism, 1.71 g (10 mmol) of 4-trifluoromethylbenzonitrile, 10 ml of methanol and 50 mg (0.5 mmol) of a 60 wt % nickel-silica were weighed, and hydrogen gas was introduced at 5 kg/cm²G. The mixture was quickly heated to 120° C., and stirred while gradually supplying hydrogen so as to keep the total pressure at 10 kg/cm²G. Six hours after, the reaction was terminated, the catalyst was removed by filtration, and the collected reaction solution was analyzed by gas chromatography, which revealed the production of 4-trifluoromethylbenzylamine in a 77.8% yield.

Example 13

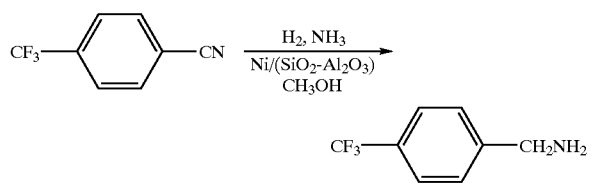

In a 50-ml autoclave with an electromagnetic stirring mechanism, 1.71 g (10 mmol) of 4-trifluoromethylbenzonitrile, 10 ml of a 2M ammoniacal methanol solution (ammonia 20 mmol) and 50 mg (0.5 mmol) of a 65 wt % nickel-silica alumina were weighed, and hydrogen gas was introduced at 5 kg/cm²G. The mixture was quickly heated to 120° C., and stirred while gradually supplying hydrogen so as to keep the total pressure at 10 kg/cm²G. Six hours after, the reaction was terminated, the catalyst was removed by filtration, and the collected reaction solution was analyzed by gas chromatography, which revealed the production of 4-trifluoromethylbenzylamine in a 98.6% yield.

Example 14

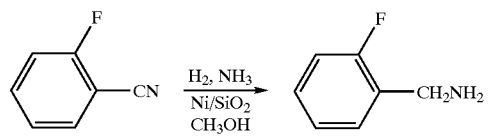

In a 50-ml autoclave with an electromagnetic stirring mechanism, 1.21 g (10 mmol) of 2-fluorobenzonitrile, 10 ml of a 2M ammoniacal methanol solution (ammonia 20 mmol) and 50 mg (0.5 mmol) of a 60 wt % nickel-silica were weighed, and hydrogen gas was introduced at 5 kg/cm²G. The mixture was quickly heated to 120° C., and stirred while gradually supplying hydrogen so as to keep the total pressure at 10 kg/cm²G. Six hours after, the reaction was terminated, the catalyst was removed by filtration, and the collected reaction solution was analyzed by gas chromatography, which revealed the production of 2-fluorobenzylamine in a 98.1% yield.

Example 15

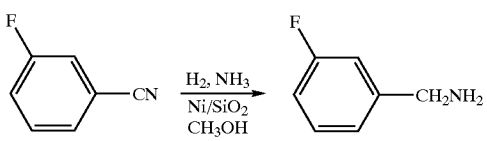

In a 50-ml autoclave with an electromagnetic stirring mechanism, 1.21 g (10 mmol) of 3-fluorobenzonitrile, 10 ml of a 2M ammoniacal methanol solution (ammonia 20 mmol) and 50 mg (0.5 mmol) of a 60 wt % nickel-silica were weighed, and hydrogen gas was introduced at 5 kg/cm²G. The mixture was quickly heated to 120° C., and stirred while gradually supplying hydrogen so as to keep the total pressure at 10 kg/cm²G. Six hours after, the reaction was terminated, the catalyst was removed by filtration, and the collected reaction solution was analyzed by gas chromatography, which revealed the production of 3-fluorobenzylamine in a 86.5% yield.

Example 16

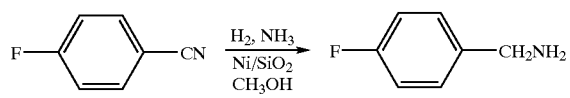

In a 50-ml autoclave with an electromagnetic stirring mechanism, 1.21 g (10 mmol) of 4-fluorobenzonitrile, 10 ml of a 2M ammoniacal methanol solution (ammonia 20 mmol) and 50 mg (0.5mmol) of a 60 wt % nickel-silica were weighed, and hydrogen gas was introduced at 5 kg/cm²G. The mixture was quickly heated to 120° C., and stirred while gradually supplying hydrogen so as to keep the total pressure at 10 kg/cm²G. Six hours after, the reaction was terminated, the catalyst was removed by filtration, and the collected reaction solution was analyzed by gas chromatography, which revealed the production of 4-fluorobenzylamine in a 99.5% yield.

Example 17

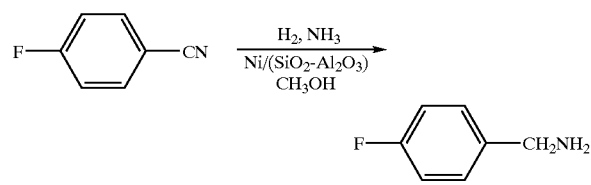

In a 50-ml autoclave with an electromagnetic stirring mechanism, 1.21 g (10 mmol) of 4-fluorobenzonitrile, 10 ml of a 2M ammoniacal methanol solution (ammonia 20 mmol)

and 50 mg (0.5 mmol) of a 65 wt % nickel-silica alumina were weighed, and hydrogen gas was introduced at 5 kg/cm²G. The mixture was quickly heated to 120° C., and stirred while gradually supplying hydrogen so as to keep the total pressure at 10 kg/cm²G. Six hours after, the reaction was terminated, the catalyst was removed by filtration, and the collected reaction solution was analyzed by gas chromatography, which revealed a quatitative production of 4-fluorobenzylamine.

Example 18

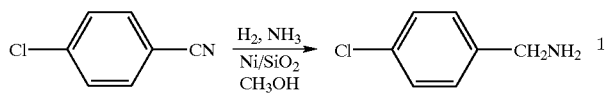

In a 50-ml autoclave with an electromagnetic stirring mechanism, 1.37 g (10 mmol) of 4-chlorobenzonitrile, 10 ml of a 2M ammoniacal methanol solution (ammonia 20 mmol) and 50 mg (0.5 mmol) of a 60 wt % nickel-silica were weighed, and hydrogen gas was introduced at 5 kg/cm²G. The mixture was quickly heated to 120° C., and stirred while gradually supplying hydrogen so as to keep the total pressure at 10 kg/cm²G. Six hours after, the reaction was terminated, the catalyst was removed by filtration, and the collected reaction solution was analyzed by gas chromatography, which revealed the production of 4-chlorobenzylamine in a 88.2% yield.

Example 19

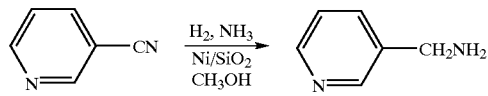

In a 10-ml autoclave, 0.104 g (1.00 mmol) of 3-cyanopyridine, 1 ml of a 2M ammoniacal methanol solution (ammonia 2 mmol) and 5 mg (0.05 mmol) of a 60 wt % nickel-silica were weighed, and hydrogen gas was introduced at 10 kg/cm²G. The mixture was stirred at 120° C. for six hours. The obtained reaction solution was analyzed by gas chromatography, which revealed the production of 3-aminomethylpyridine in a 85.6% yield.

Example 20

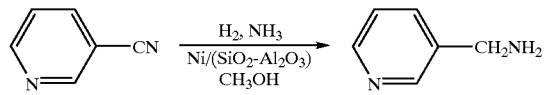

In a 10-ml autoclave, 0.104 g (1.00 mmol) of 3-cyanopyridine, 1 ml of a 2M ammoniacal methanol solution (ammonia 2 mmol) and 5 mg (0.05 mmol) of a 65 wt % nickel-silica alumina were weighed, and hydrogen gas was introduced at 10 kg/cm²G. The mixture was stirred at 120° C. for six hours. The obtained reaction solution was analyzed by gas chromatography, which revealed the production of 3-aminomethylpyridine in a 84.2% yield.

Example 21

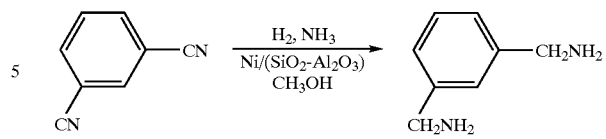

In a 10-ml autoclave, 0.128 g (1.00 mmol) of isophthalonitrile, 6 ml of a 2M ammoniacal methanol solution (ammonia 12 mmol) and 5 mg (0.05 mmol) of a 65 wt % nickel-silica alumina were weighed, and hydrogen gas was introduced at 15 kg/cm²G. The mixture was stirred at 170° C. for one hour. The obtained reaction solution was analyzed by gas chromatography, which revealed the production of m-xylylenediamine in a 81.7% yield.

Example 22

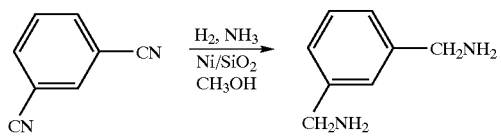

In a 10-ml autoclave, 0.128 g (1.00 mmol) of isophthalonitrile, 6 ml of a 2M ammoniacal methanol solution (ammonia 12 mmol) and 5 mg (0.05 mmol) of a 60 wt % nickel-silica were weighed, and hydrogen gas was introduced at 15 kg/cm²G. The mixture was stirred at 170° C. for two hours. The obtained reaction solution was analyzed by gas chromatography, which revealed the production of m-xylylenediamine in a 79.5% yield.

Example 23

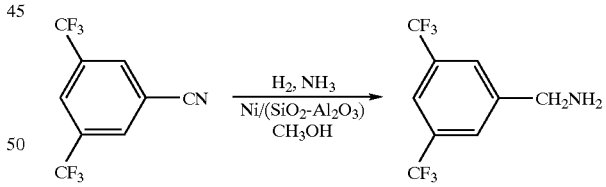

In a 50-ml autoclave with an electromagnetic stirring mechanism, 2.39 g (10 mmol) of 3,5-bis(trifluoromethyl) benzonitrile, 10 ml of a 2M ammoniacal methanol solution (ammonia 20 mmol) and 50 mg (0.5 mmol) of a 65 wt % nickel-silica alumina were weighed, and hydrogen gas was introduced at 5 kg/cm²G. The mixture was quickly heated to 120° C., and stirred while gradually supplying hydrogen so as to keep the total pressure at 10 kg/cm²G. Six hours after, the reaction was terminated, the catalyst was removed by filtration, and the collected reaction solution was analyzed by gas chromatography, which revealed the production of 3,5-bis(trifluoromethyl)benzylamine in a 71.4% yield.

Example 24

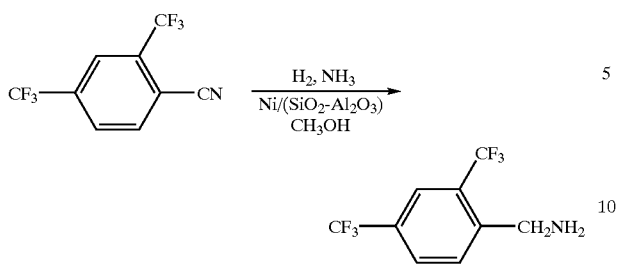

In a 50-ml autoclave with an electromagnetic stirring mechanism, 2.39 g (10 mmol) of 2,4-bis(trifluoromethyl)benzonitrile, 10 ml of a 2M ammoniacal methanol solution (ammonia 20 mmol) and 50 mg (0.5 mmol) of a 65 wt % nickel-silica alumina were weighed, and hydrogen gas was introduced at 5 kg/cm$^2$G. The mixture was quickly heated to 120° C., and stirred while gradually supplying hydrogen so as to keep the total pressure at 10 kg/cm$^2$G. Six hours after, the reaction was terminated, the catalyst was removed by filtration, and the collected reaction solution was analyzed by gas chromatography, which revealed the production of 2,4-bis(trifluoromethyl)benzylamine in a 82.2% yield.

Example 25

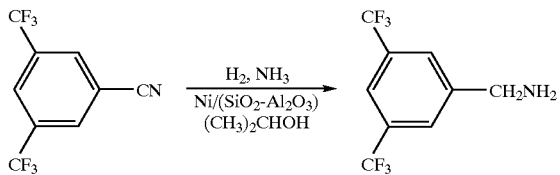

In a 50-ml autoclave with an electromagnetic stirring mechanism, 2.39 g (10 mmol) of 3,5-bis(trifluoromethyl)benzonitrile, 10 ml of a 2M ammoniacal 2-propanol solution (ammonia 20 mmol) and 50 mg (0.5 mmol) of a 65 wt % nickel-silica alumina were weighed, and hydrogen gas was introduced at 5 kg/cm$^2$G. The mixture was quickly heated to 120° C., and stirred while gradually supplying hydrogen so as to keep the total pressure at 10 kg/cm$^2$G. Six hours after, the reaction was terminated, the catalyst was removed by filtration, and the collected reaction solution was analyzed by gas chromatography, which revealed the production of 3,5-bis(trifluoromethyl)benzylamine in a 85.2% yield.

Example 26

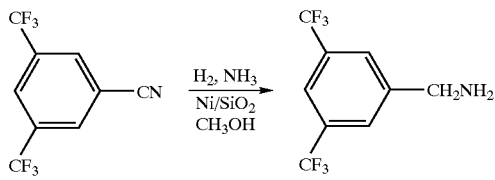

In a 10-ml, stainless-steel-made autoclave, 0.120 g (0.50 mmol) of 3,5-bis(trifluoromethyl)benzonitrile, 2.5 mg (0.025 mmol) of a 60 wt % nickel-silica and 1 ml of a 2M ammoniacal methanol solution (ammonia 2 mmol) were weighed, the atmosphere of the system was thoroughly substituted with hydrogen gas, and hydrogen gas was introduced so as to attain a partial pressure of 10 kg/cm$^2$G. The mixture was heated to 140° C. under stirring, and subjected to hydrogenation for one hour. Upon completion of the reaction, the autoclave was cooled to the room temperature, hydrogen gas was purged out to recover the normal pressure, and the reaction solution was taken out. The collected reaction solution was analyzed by gas chromatography, which revealed the production of 3,5-bis(trifluoromethyl)benzylamine in a 81.2% yield.

Example 27

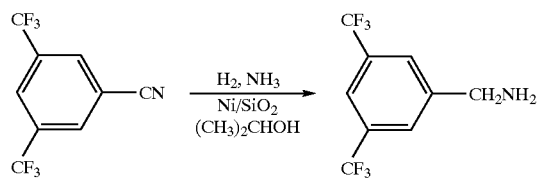

In a 10-ml, stainless-steel-made autoclave, 0.120 g (0.50 mmol) of 3,5-bis(trifluoromethyl)benzonitrile, 2.5 mg (0.025 mmol) of a 60 wt % nickel-silica and 1 ml of a 2M ammoniacal 2-propanol solution (ammonia 2 mmol) were weighed, the atmosphere of the system was thoroughly substituted with hydrogen gas, and hydrogen gas was introduced so as to attain a partial pressure of 10 kg/cm$^2$G. The mixture was heated to 120° C. under stirring, and subjected to hydrogenation for two hours. Upon completion of the reaction, the autoclave was cooled to the room temperature, hydrogen gas was purged out to recover the normal pressure, and the reaction solution was taken out. The collected reaction solution was analyzed by gas chromatography, which revealed the production of 3,5-bis(trifluoromethyl)benzylamine in a 92.1% yield.

INDUSTRIAL APPLICABILITY

The present invention can provide a method for producing, through hydrogenation of aromatic nitriles under low-pressure conditions, industrially valuable aromatic primary amines which are available in a variety of fields such as those of medicine, agricultural chemical, dye, surfactant and chemical agent.

What is claimed is:

1. A method for producing an aromatic primary amine, characterized by hydrogenating an aromatic nitrile at a low partial pressure of hydrogen in a heterogeneous system comprising a non-reductive polar solvent and a nickel-immobilized catalyst suspended therein.

2. A method as claimed in claim 1, wherein a carrier of said immobilized nickel catalyst is selected from the group consisting of silica, alumina, activated carbon and any combinations thereof.

3. A method as claimed in claim 1, wherein said non-reductive polar solvent comprises an alcoholic solvents.

4. A method as claimed in claim 1, wherein said partial pressure of hydrogen is suppressed to a level of 19 kg/cm$^2$G or below.

5. A method as claimed in claim 1, wherein said aromatic nitrile has a substituent on the aromatic ring thereof.

6. A method as claimed in claim 1, wherein said hydrogenation carried out in the presence of ammonia.

7. A method as claimed in claim 2, wherein said non-reductive polar solvent is anrom alcoholic solvents.

8. A method as claimed in claim 2, wherein said partial pressure of hydrogen is suppressed to a level of 19 kg/cm$^2$G or below.

9. A method as claimed in claim 2, wherein said aromatic nitrile has a substituent on the aromatic ring thereof.

10. A method as claimed in claim 2, wherein said hydrogenation is carried out in the presence of ammonia.

11. A method as claimed in claim 3, wherein said partial pressure of hydrogen is suppressed to a level of 19 kg/cm$^2$G or below.

12. A method as claimed in claim 3, wherein said aromatic nitrile has a substituent on the aromatic ring thereof.

13. A method as claimed in claim 3, wherein said hydrogenation is carried out in the presence of ammonia.

14. A method as claimed in claim 4, wherein said aromatic nitrile has a substituent on the aromatic ring thereof.

15. A method as claimed in claim 4, wherein said hydrogenation is carried out in the presence of ammonia.

16. A method as claimed in claim 5, wherein said hydrogenation is carried out in the presence of ammonia.

* * * * *